US008524468B2

(12) United States Patent
Edberg

(10) Patent No.: US 8,524,468 B2
(45) Date of Patent: *Sep. 3, 2013

(54) METHOD FOR DETECTING THE PRESENCE OR ABSENCE OF METHICILLIN RESISTANT STAPHYLOCOCCUS AUREUS (MRSA) IN A TEST SAMPLE

(75) Inventor: Stephen C. Edberg, Belleair Bluffs, FL (US)

(73) Assignee: Pilots Point LLC, Sarasota, FL (US)

( * ) Notice: Subject to any disclaimer, the term of this patent is extended or adjusted under 35 U.S.C. 154(b) by 482 days.

This patent is subject to a terminal disclaimer.

(21) Appl. No.: 12/653,946

(22) Filed: Dec. 22, 2009

(65) Prior Publication Data

US 2011/0151495 A1 Jun. 23, 2011

(51) Int. Cl.
*C12Q 1/04* (2006.01)
(52) U.S. Cl.
USPC .......................................................... 435/34
(58) Field of Classification Search
None
See application file for complete search history.

(56) References Cited

U.S. PATENT DOCUMENTS

| | | | |
|---|---|---|---|
| 4,035,238 A * | 7/1977 | Meyer et al. ................ | 435/6.16 |
| 6,022,682 A | 2/2000 | Mach et al. | |
| 6,548,268 B1 | 4/2003 | Rambach | |
| 7,087,401 B2 | 8/2006 | Sandberg et al. | |
| 7,335,485 B2 | 2/2008 | Black et al. | |
| 2005/0124026 A1 | 6/2005 | Walsh et al. | |
| 2006/0019330 A1 | 1/2006 | Lakshmi et al. | |
| 2009/0191577 A1 | 7/2009 | Edberg | |
| 2011/0151495 A1 | 6/2011 | Edberg | |
| 2011/0269160 A1 | 11/2011 | Edberg | |
| 2011/0269163 A1 | 11/2011 | Edberg | |

FOREIGN PATENT DOCUMENTS

| | | |
|---|---|---|
| WO | 9855644 | 12/1998 |
| WO | 9950438 | 8/1999 |
| WO | 0053799 | 9/2000 |

OTHER PUBLICATIONS

Bayliss et al."Plasma coagulation by microorganisms other than *Staphylococcus aureys*". Journal of Bacteriology. 1965, vol. 89, No. 1, pp. 101-105.*
Jordens et al. J Med Microbiol. 1989, vol. 30, pp. 245-252.*
Freydiere et al. "Staphychrom 2, a new specific staphylocoagulase test using a chromogenic substrate". Clinical Microbiology and Infection, 2002, vol. 8, supplement 1, p392,.*
Loulergue et al. "Evaluation of a new chromogenic medium for isolation and presumptive identification of methicillin resistant *Staphylococcus aureus* from human clinical specimens". Eur J Clin Microbiol Infect Dis., 2006, 25(6), pp. 407-409.*
Perry et al. "Evaluation of S. auereus ID, a New Chromogenic Agar Medium for Detection of *Staphylococcus aureus*", Journal of Clinical Microbiology, vol. 41, No. 12, Dec. 2003, p. 5695-5698.

Clancy, "Active Screening in High-Risk Units Is an Effective and Cost-Avoidant Method to Reduce the Rate of Methicillin-Resistant *Staphylococcus aureus* Infection in the Hospital", Infection Control and Hospital Epidemiology, Oct. 2006, vol. 27, No. 10, p. 1009-1017.
Baird et al. 'Media used in the Detection and Enumeration of Staphylococcus', International Journal of Food Microbiology, 1995, vol. 26, p. 209-211.
Perry et al., 'Development and Evaluation of a Chromogenic Agar Medium for methicillin-resistant *Staphylococcus aureus*', Journal of Clinical Microbiology, 2004, vol. 42, p. 4519-4523.
Stevens et al., "Use of trehalose-mannitol-phosphatase agar to differentiate *Staphylococcus epidermidis* and *Staphylococcus saprophyticus* from other coagulase-negative staphylococci", Journal of Clinical Microbiology, 1984, vol. 20, p. 977-980.
Yazdankhah et al., "Simple and Direct Detection of *Staphylococcus aureus* in Milk by a Tube Coagulase Test", Letters in Applied Microbiology, vol. 27, No. 2, 1998, p. 111-115.
Selepak et al., "Inoculum Size and Lot-to-Lot Variation as Significant Variables in the Tube Coagulase Test for *Staphylococcus-aureus*", Journal of Clinical Microbiology, vol. 22, No. 5, 1985, p. 835-837.
Boothby et al., "Tandem Coagulase Thermo Nuclease Agar Method for the Detection of *Staphylococcus-aureus*", vol. 37, No. 2, 1979, p. 298-302.
Chang et al., "Evaluation of a Latex Agglutination Test for Rapid Identification of *Staphylococcus aureus* from Foods", vol. 56, No. 9, 1993, p. 759-762.
Lominski et al. "An Improved Direct Coagulase Test for the Rapid Detection of *Staphylococcus aureus*", British Medical Journal 1948, vol. 116, No. 4546, p. 343.
Varettas et al. "Anticoagulant Carryover May Influence Clot Formation in Direct Tube Coagulase Tests from Blood Cultures," Journal of Clinical Microbiology, vol. 43, No. 9, Sep. 2005, pp. 4613-4615.
Carret et al. "Relative Value of Staphlyo Coagulase and Fibrinogen Affinity for the Identification of *Staphylococcus-aureus*", Journal of Applied Bacteriology, vol. 53, No. 3, 1982, pp. 351-354.
Carey et al. "The Combined Oxacillin Resistance of Coagulase (CORC) Test for Rapid Identification and Prediction of Oxacillin Resistance in Staphylococcus Species Directly from Blood Culture", Journal of Clinical Pathology, vol. 61, No. 7, Jul. 1, 2008, pp. 866-868.

(Continued)

*Primary Examiner* — Vera Afremova
(74) *Attorney, Agent, or Firm* — O'Shea Getz P.C.

(57) ABSTRACT

A dry mixture, a liquid menstrum, and a method, are described for use in detecting the presence or absence of Methicillin Resistant *Staphylococcus aureus* ("MRSA") in a first generation biological or environmental specimen sample. First generation specimen samples that can be analyzed include nasal swabs, lesion swabs, skin swabs, throat swabs, food swabs, tanning salon swabs, gym swabs, restaurant swabs, hotel swabs, and the like. The menstrum and method include an anti-ribosomal antibiotic component that will selectively prevent Methicillin Susceptible *Staphylococcus aureus* ("MSSA") from growing in the menstrum, while allowing MRSA to grow in the menstrum. The menstrum also includes components which will stimulate growth of MRSA, plus coagulase reacting factors which will cause the menstrum to clot in the event that MRSA is present in the sample. The menstrum also includes components which will produce a detectable signal in the clot, which signal indicates the presence of MRSA in the sample.

9 Claims, 1 Drawing Sheet

(56) References Cited

OTHER PUBLICATIONS

Bottone et al. "Rapid Detection and Identification of Methicillin-Resistant *Staphylococcus aureus* Directly from Positive Blood Cultures Exhibiting Gram-Positive Cocci in Clusters", Clinical Microbiology ewsletter, vol. 29, No. 18, Aug. 31, 2007, pp. 137-139.

Smyth et al. "Mannitol Salt Agar-Cefoxitin Combination as a Screening Medium for Methicillin-Resistant *Staphylococcus aureus*", Journal of Clinical Microbiology, Aug. 2005, vol. 43, No. 8, pp. 3797-3799.

McDonald et al. "Rapid Identification of *Staphylococcus aureus* from Blood Culture Bottles by a Classic 2-Hour Tube Coagulase Test", Journal of Clinical Microbiology, Jan. 1995, p. 50-52.

Goldstein et al. "Microtube Coagulase Test for Detection of Coagulase-Positive Staphylococci", Journal of Clinical Microbiology, May 1982, p. 848-851.

Hauschild et al. "A Modified Pork Plasma Agar for the Enumeration of *Staphylococcus aureus* in foods", Canadian Journal of Microbiology, vol. 25, Jun. 4, 1979, p. 1052-1057.

Lindberg et al. "High Rate of Transfer of *Staphylococcus aureus* from Parental Skin to Infant Gut Flora", Journal of Clinical Microbiology, vol. 42, No. 2, Feb. 2004, p. 530-534.

Bascomb, S., et al. "Use of Enzyme Tests in Characterization and Identification of Aerobic and Facultatively Anaerobic Gram-Positive Cocci", Journal of Clinical Microbiology Reviews, vol. 11, No. 2, Apr. 1988, p. 318-340.

Kloos, W.E., et al. Journal of Clinical Microbiology, "Identification of Staphylococcus Species with the API STAPH-IDENT System", vol. 16, No. 3, Sep. 1982, p. 509-516.

Remel, Inc., "RapID™ STAPH PLUS System", IFU 831 1009, Rev. Jan. 4, 2007, p. 2-6.

Rambach, A., BD Diagnostics, BBL CHROMagar, "A Lean Approach to Testing", Feb. 2007, p. 2-14.

Lindsey, J.A., et al. "Indentification of *Staphylococcus epidermidis* and *Staphyloccus hominis* from Blood Cultures by Testing Susceptibility to Desferrioxamine", European Journal of Microbiology & Infectious Diseases, 12:127-131 (1993).

\* cited by examiner

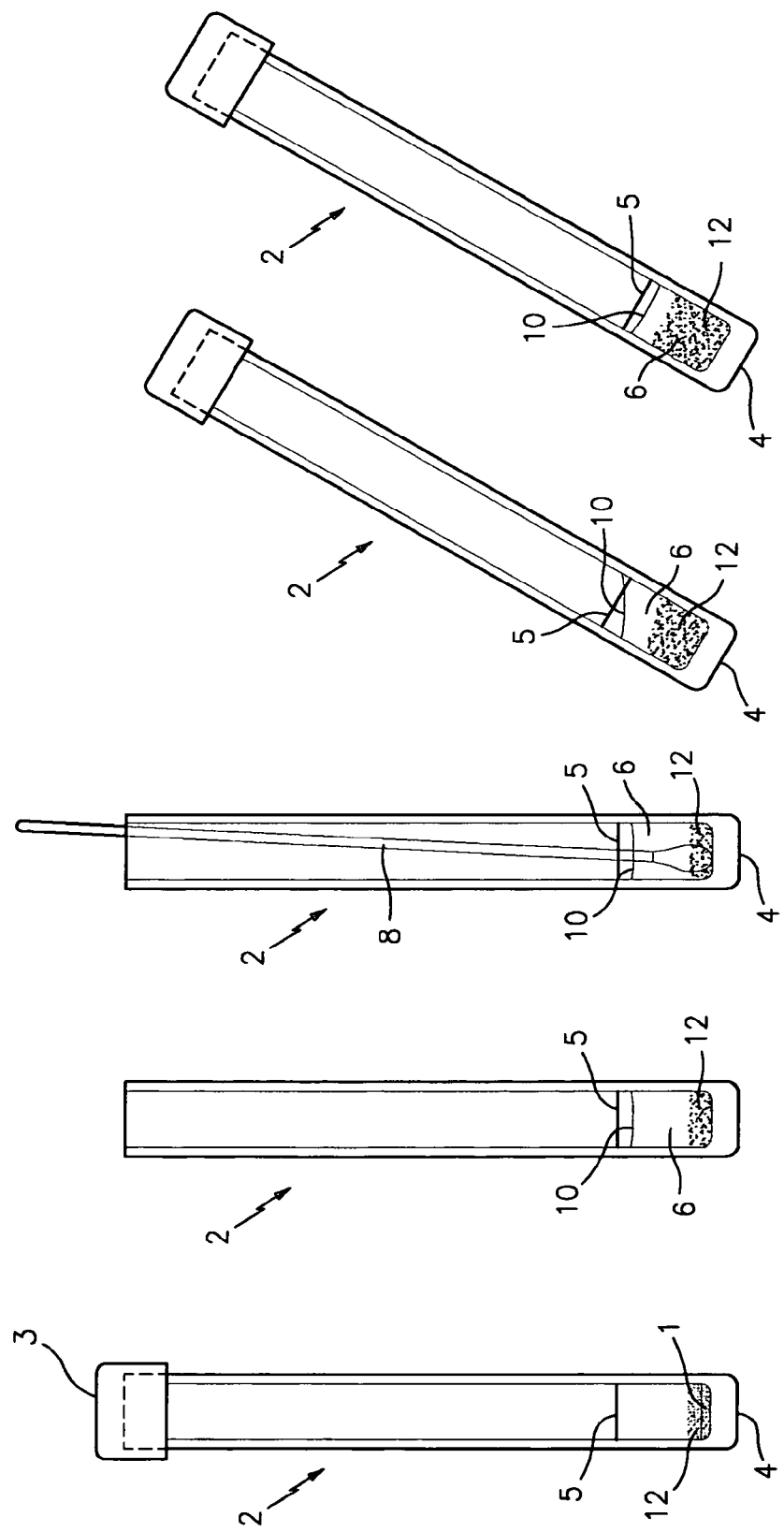

METHOD FOR DETECTING THE PRESENCE OR ABSENCE OF METHICILLIN RESISTANT STAPHYLOCOCCUS AUREUS (MRSA) IN A TEST SAMPLE

TECHNICAL FIELD

The present method and test mixture relates to the detection of *Staphylococcus aureus* in a biological, environmental, or food sample, and more particularly to those methods and test mixtures utilizing reacting factors which the target microbe(s) can convert into a clot. Drug ingredients which can prevent false positive results of the presence of Methicillin Resistant *Staphylococcus aureus* (MRSA) in the sample are also included in the testing menstrum. Examples of suitable drug ingredients include, but are not limited to, amino glycoside anti-ribosomal antibiotics, such as gentamicin, tobramycin, and kanamycin, for example, which are active against MSSA but not MRSA. When used in conjunction with a cell wall active anti microbial agent possessing methicillin-like activity, the anti-ribosomal antibiotic enhances the detection of MRSA.

BACKGROUND INFORMATION

*Staphylococcus aureus* (*S. aureus*) can be a virulent pathogen of animals and humans. Moreover, it can cause severe food poisoning by the production of a toxin. Diseases caused by *S. aureus* cover a very wide clinical spectrum, from simple skin infections to life threatening infections of the bones, heart, and organs. Of particular concern is the recognition that *S. aureus* infection is common after surgery. It is also associated with intravenous tubing and other implants.

The bacterium *S. aureus* may be transmitted between healthy individuals by skin to skin contact, by fomites from the nose to the skin or surgical site, or from a commonly shared item or a surface (e.g., tanning beds, gym equipment, food handling equipment, etc.) where the transfer may be made to a subsequent person who uses the shared item or touches the surface. Of great medical concern is the recognition that healthy people entering hospitals may "carry" *S. aureus* (e.g., on their skin, or in their noses, etc.) without any signs or symptoms that they do so. In the presence of favorable conditions (often found in but not limited to hospitals), the *S. aureus* can activate and cause serious infection. In addition, *S. aureus* can also be a source of food poisoning, often caused by a food handler contaminating the food product (e.g., meat, poultry, eggs, salads containing mayonnaise, bakery products, dairy products, etc.).

There are two categories of *S. aureus* based on an individual clone's susceptibility to the class of antibiotics of which methicillin is the prototype. These are referred to as methicillin susceptible *S. aureus* (MSSA), and methicillin resistant *S. aureus* (MRSA) in so far as the antibiotic has methicillin-type activity. Until only a few years ago, MRSA was most commonly found in hospitals. Now, it is frequently also present in the noses, skin, etc. of people in the non-hospital community. Moreover, these MRSA bacteria are increasingly causing serious infections in the community. MRSA is particularly serious because only very few antibiotics (e.g., vancomycin) have been shown to be uniformly effective against MRSA.

The Center for Disease Control and Prevention actively surveys for the development of methicillin resistant *S. aureus*. In 2000, the Society for Healthcare Epidemiology of America guidelines recommended contact isolation for patients with MRSA. In addition to the morbidity and mortality caused by MRSA, it has been estimated that each case of infection costs at least $23,000. Accordingly, many hospitals and nursing homes proactively sample patients for MRSA [Clany, M., Active Screening in High-Risk units is an effective and cost-avoidant method to reduce the rate of methicillin-resistant *Staphylococcus aureus* infection in the hospital. Infection Control and Hospital Epidemiology 27: 1009-1017, 2006].

Meyer et al. (U.S. Pat. No. 4,035,238) describes the use of a broth for the detection of *S. aureus* that utilized mannitol as a source of carbon and DNA methyl green as an indicator. Neither of these chemicals are coagulase reactive substrates.

Rambach (U.S. Pat. No. 6,548,268) employs at least two chromogenic agents in an agar menstrum: 5-bromo-6-chloro-indoxyl-phosphate; and 5-bromo-4-chloro-3-indoxyl glucose in the presence of deferoxamine. An individual colony hydrolyzing these substrates will produce colors that will mix with each other and not be independent of one another.

A large number of classical agar-based culturing procedures are utilized to detect MSSA and MRSA from human, animal, food, etc. samples. They have in common a basic menstrum with chemical inhibitors such as 6-8% sodium chloride, potassium tellurite, and a variety of antibiotics. For example Stevens and Jones described the use of a trehalose-mannitol-phosphatase agar [Stevens, D L and Jones, C. "Use of trehalose-mannitol-phosphatase agar to differentiate *Staphylococcus epidermidis* and *Staphylococcus saprophyticus* from other coagulase-negative staphylococci", J. of Clin. Microbiology 20:977-980, 1984]. The use of mannitol as an energy source and sodium chloride as a selective agent into an agar known as mannitol-salt agar has been commonly used in clinical laboratories [Baird, R. M. and W. H. Lee., Media used in the detection and enumeration of *Staphylococcus aureus*, Int. J. Food Microbiology. 26:209-211, 1995]. Within the prior art of culturing, it is a generally accepted procedure to perform coagulase tests utilizing samples suspicious of being *S. aureus* bacterial colonies that are first isolated in a pure culture.

The procedure "*S. aureus* ID" [Bio Merieux, La Balme Les Grottes, France] uses an alpha-glucosidase substrate in agar to detect *S. aureus*. A single substrate is utilized. [Perry, J. D. et al., "Evaluation of *S. aureus* ID, a new chromogenic agar menstrum for detection of *Staphylococcus aureus*", J. Clin. Microbiology 41:5695-5698, 2003]. A variant of this menstrum, which contains added antibiotics and sodium chloride, is designed to detect MRSA [Perry et al., "Development and evaluation of a chromogenic agar menstrum for methicillin-resistant *Staphylococcus aureus*", J. of Clin. Micro. 42:4519-4523, 2004].

Selepak and Witebsky disclose a study evaluating the inoculum size and lot-to-lot variability of the tube coagulase test for *S. aureus*. Specimens were collected and isolates were generated from the bacterial colonies on agar plates. Tubes containing anticoagulated rabbit coagulase plasma were inoculated with a part of, or more than one, staphylococcal colony from the isolates. The tubes were incubated and examined for the presence of clot. According to Selepak and Witebsky, "with some isolates and some lots of coagulase plasma, even a single colony [from the isolate] may not provide enough inoculum for a positive coagulase test". Furthermore, Selepak and Witebsky state that "[e]expressed more quantitatively, at least 8 log 10 organisms per ml should be used whenever possible for each coagulase tube test. Our data further suggest that *S. aureus* does not grow in coagulase plasma; therefore, the incubation of coagulase plasma for 18 to 24 h does not compensate for the use of small inoculum.". Thus, Selepak and Witebsky indicate that it is impractical, if not impossible, to detect the presence or absence of *S. aureus* in first generation biological specimen samples using a direct coagulase test. [Selepak, S. T et al, "Inoculum Size and Lot-to-Lot Variation as Significant Variables in the Tube Coagulase Test for *Staphylococcus aureus*", Journal of Clin. Microbiology, November 1985, p. 835-837].

It would, therefore, be desirable to provide a test mixture and a method that can rapidly detect MRSA directly from a first generation sample, one that does not require a skilled technician to perform the method, one that can be performed without the need to develop isolates from the specimen sample (i.e., one that can be performed on a "first generation" specimen sample), and one that, unlike the teachings of Selepak and Witbsky, does not require a large concentration of *S. aureus* organisms to be of use from a first generation specimen.

SUMMARY OF THE INVENTION

This invention relates to a method and test mixture for specific detection of MRSA bacteria in a first generation biological, environmental, or food sample. In the detection of MRSA, a test mixture (which mixture may also be referred to as a "menstrum") is utilized that includes coagulase substrates (sometimes referred to as "coagulase reacting factors") that react specifically with coagulase produced by *S. aureus* to form a clot, admixed with constituents that facilitate the multiplication of MRSA and additional constituents that inhibit or prevent the multiplication of MSSA in the sample. Hence, the present method and test mixture utilize coagulase substrates that are activated by the coagulase produced by *S. aureus*, and the enzyme coagulase is specific to pathogenic staphylococci, as is disclosed in the Code of The Federal Register, Title 21, Chapter 1, Sub Part C, Sec. 866.2160 "Coagulase Plasma".

MSSA growth inhibitors are included to inhibit or otherwise negatively affect MSSA bacterial growth, while not interfering with MRSA bacterial growth. The untreated sample (e.g., collected from a nasal swab from a person, or off of a surface, etc.) is added to the test mixture, and the inoculated test sample is incubated. If MRSA is present within the sample, the MRSA will preferentially metabolize and multiply within the test mixture and will elaborate and produce coagulase that reacts with the coagulase substrates. The reaction between the coagulase produced by the MRSA and the coagulase substrates within the test mixture will produce a detectable clot within the test mixture in a time period typically between two and twenty-four hours, positively indicating the presence of MRSA.

The test mixture is preferably prepared in a form that facilitates handling, packaging, storing, etc., of the test mixture. A dry powder that can be hydrated into liquid form is a particularly preferable form for the test mixture, but the present invention is not limited to a powder form. The test mixture may assume a liquid form, or any other form (e.g., paste, gel, etc.), preferably one that can be hydrated for use.

The coagulase substrates within the test mixture may be provided within a plasma, or may be provided by another substance that is operative to react with the coagulase produced by *S. aureus* to form a clot. Present testing indicates that rabbit plasma is a favorable source of a coagulase substrate. Other plasmas (e.g., pork plasma) may be used alternatively. Fibrinogen is another example of a source of a coagulase substrate. In those embodiments that utilize plasma as a source of a coagulase substrate, it may be preferable to add a non-plasma source of a coagulase substrate to the test mixture to ensure an adequate source of coagulase substrate within the test mixture. As an example, our testing indicates that combining fibrinogen and rabbit plasma within the test mixture is an effective means for ensuring a consistent, adequate source of coagulase substrates. An advantage of adding a material such as fibrinogen to the test mixture is that it increases the performance consistency of the test mixture, and makes the method less susceptible to variability that may occur with plasma.

The growth promoting constituents within the test mixture that facilitate the metabolism and multiplication of, and sustain, *S. aureus* can be varied to suit the application. Those in the art will recognize that many different combinations of constituents, and varying relative amounts of the same constituents, can be used to provide the same functionality. Growth promoting constituents include sources of nitrates and proteins, material operative to assist in the generation of nucleic acid synthesis, sources of energy for the *S. aureus*, sources of amino acid growth factor, and in some embodiments materials operable to help repair damaged target organisms. This list of growth promoting constituents does not represent all of the materials that can be beneficial within the test mixture, but does illustrate materials that are acceptable (e.g., vitamins, salts, minerals, inorganic moieties, etc.). The test mixture may include other constituents that benefit the performance of the test mixture.

In most applications of the present invention, it will be desirable to utilize a test mixture that includes the following: a) an effective amount of amino acids; b) an effective amount of nitrogen sources; c) an effective amount of salts; d) an effective amount of vitamins; e) an effective amount of calcium; and an effective amount of a hydrolyzable substrate (which could be a nutrient-indicator and/or one or more sugars) that can be metabolized by MRSA. Those skilled in the art will recognize that natural sources of such amino acids can be used rather than pure sources. The natural sources (e.g. extract of whole organisms, such as yeast) may be in mixture form or in purified form. The natural mixtures can contain varying amounts of such amino acids and vitamins. Those skilled in the art will further recognize that many different combinations of amino acids and vitamins can be used in present invention test mixture. Effective amounts of drug ingredients which selectively inhibit the growth of MSSA in the sample are also included in the testing mixture. As noted above, examples of such suitable drug ingredients include the anti-ribosomal antibiotic gentamicin, which is active against MSSA but not MRSA. Drugs in this class can inhibit protein synthesis.

Those in the art will further recognize that carbon, nitrogen, trace elements, vitamins, amino acids and selective agents can be provided in many forms. Generally, it is preferred to have an amount of vitamins and amino acids within a predetermined range, but those in the art will recognize that the actual properties of each ingredient may be varied so that reduction in the amount of one ingredient can be compensated by an increase in the amount of another. This is particularly relevant when the essential amino acids, trace elements or vitamins of the microbes sought to be detected are known. Some ingredients may be provided in reduced amounts or deleted if they may be synthesized endogenously by the microorganism whose presence is to be determined. Salts may be provided as a source of ions upon dissociation.

The test mixture may be packaged in a container (e.g., a test tube, a container with a flat bottom wall, etc.) that facilitates the testing process. If the menstrum is prepared in a form that can be hydrated, the mixture can be hydrated with sterile water or non-sterile water.

To detect the presence of MRSA within a sample, the sample is obtained from a biological, environmental, or food specimen. A sample collected using a nasal swab is an example of a first generation sample that is particularly convenient to collect and test using the present invention. Once collected, the sample is inoculated into the test mixture.

The inoculated sample is incubated under conditions favorable to facilitate the multiplication of MRSA that may be present within the inoculated sample, while suppressing the multiplication of MSSA that may be present in the sample. In the case of a powdered test mixture hydrated with water, the incubation may be carried out at temperatures between about 20° C. to 42° C. The combination of sequential enzyme specificity, MRSA enhancing growth factors, and an MSSA suppressing antibiotic(s), selectivity, provides multiple hurdles which prevent the competing non-target bacteria from being detected within the test period; e.g. 24 hours or less.

The present invention test and method can be used in hospital admissions, routinely in intensive care units, in nursing homes, dialysis patients, people receiving home immunosuppressive therapy, and the like. It can also be used in environmental settings (e.g., gyms, tanning salons, restaurants, etc.) where the bacteria MRSA may be transferred from a human carrier and it can be used to test various different foods for MRSA contamination. It will be appreciated that a substantial benefit of the present method and mixture is that they may be performed/used without the need for expensive equipment or skilled medical technologists. Another substantial benefit of the present method/mixture is that it is operable with a relatively small amount of MRSA within the test sample; e.g., the present method/mixture has detected MRSA in samples having concentrations of MRSA as low as 100 CFU/ml.

BRIEF DESCRIPTION OF THE DRAWINGS

Details of the invention will become more readily apparent from the following detailed description of several embodiments of the invention when taken in conjunction with the accompanying drawings in which:

FIG. 1 is a side elevational view of a test tube containing a powder culturing mixture which is formulated to detect the presence or absence of S. aureus in a first generation biological sample of a nasal swab;

FIG. 2 is a side elevational view of the test tube of FIG. 1, but showing the culturing mixture having been hydrated by water;

FIG. 3 is a side elevational view of the test tube FIG. 2 and showing a cotton swab inserted into the test tube to deposit a first generation biological specimen nasal swab in the menstrum;

FIG. 4 is a side elevational view of the test tube of FIG. 3 after the specimen has been deposited and cultured in the menstrum for a period of time and indicating the absence of MRSA in the specimen; and FIG. 5 is a side elevational view similar to FIG. 4 but showing the test tube menstrum after the culturing period and indicating the presence of MRSA in the specimen.

DETAILED DESCRIPTION OF SPECIFIC EMBODIMENTS OF THE INVENTION

FIG. 1 is a side elevational view of a test tube denoted by the numeral 2 which preferably has a flat bottom 4 and a top closure 3, and which contains a dry powdered test mixture 1 which is formed in accordance with this invention for detecting the presence or absence of S. aureus in a sample; e.g., a first generational biological sample. The tube 2 is also provided with a reference line 5 which indicates the amount of water to be added to the tube 2 in order to properly hydrate the powdered mixture 1 for specimen sample testing.

Acceptable hydrated test mixtures can be made using the following constituents in the ranges indicated, to create 15 ml of test mixture:

| Constituent | Quantity per 15 ml of Test Mixture | Range per 15 ml Test Mixture |
|---|---|---|
| Nitrate Broth | 7.5 ml | 1.0 ml-9.0 ml |
| Water | 7.5 ml | 1.0 ml-9.0 ml |
| Uracil | 10.0 mg | 1.0 mg-20.0 mg |
| Sodium Pyruvate | 10.0 mg | 1.0 mg-20.0 mg |
| L-glutamine | 20.0 mg | 5.0 mg-40.0 mg |
| Sodium Sulfite | 1.0 mg | 0.5 mg-2.0 mg |
| Rabbit Plasma | 100.0 mg | 15.0 mg-500.0 mg |
| Fibrinogen | 100.0 mg | 15.0 mg-500.0 mg |
| Gentamicin | 15 mcg | 10 mcg-20 mcg |
| Hydrolyzable substrate | 500 mg | 200-800 mg |
| Sugars | 15 gm | 10-25 gm |

One effective hydrolyzable substrate is ONP-alpha-d-glucopyranoside; and effective sugars include trehalose and mannitol.

The specific examples of the constituent quantities per 15 ml of test mixture provided above represent an effective test mixture formulation that was tested and found to perform effectively. This specific example does not represent all test mixture formulations, and the present invention is not limited thereto. As stated above, those in the art will recognize that many different combinations of constituents, and varying effective amounts of the same, can be used to provide the same functionality. Hence, the present method and mixture contemplates that a number of different constituent formulations can be made. If MRSA is present in the sample being tested using the above formulation, its presence will be indicated by the formation of a clot in the sample and the presence of the color yellow in the clot.

As noted in FIG. 2, the powdered mixture 1 is properly hydrated by the addition of water, preferably distilled water, to form a hydrated test mixture 6 into which the sample (e.g., carried on a nasal swab) is deposited.

First generational test samples can be collected by a variety of different techniques; e.g., a human sample can be collected by wiping a swab within the nose of a subject. Nasal swabs are a particularly convenient way of collecting a test sample, but they are not the only collection method; e.g., test samples can be collected from throat swabs, skin lesions, undamaged skin, etc. First generational environmental samples can be collected by various known methods for example, by wiping or swabbing a surface using a dry or wet wipe/swab. Likewise, first generational food samples can be collected from the food itself, or wiping food residue from surfaces in contact with the food, etc. Once the sample is collected, it can be deposited in the hydrated test mixture 6 by using the same preferably rayon or dacron swab 8 which has been used to gather the first generation sample from the source thereof. Once the specimen sample is deposited in the test mixture 6, it is incubated within the test mixture for a period of time typically less than twenty-four hours. The incubation may occur at any temperature that is acceptable under the circumstances. After the inoculation period, the test tube 2 holding the inoculated test mixture can be inspected for the presence of a clot. The test tube 2 can be tilted to one side as shown in FIGS. 4 and 5 to see if the meniscus 10 of the text mixture will move or whether a clot keeps the test mixture below a reference line 5. The presence of a clot indicates that MRSA may be present in the test sample, and the absence of a clot in the inoculated test mixture indicates that *S. aureus* is not present in the test mixture 6, as shown in FIG. 4. In some instances, the entire inoculated test mixture will clot, and in others some liquid will remain in the container with the clot. Approximately 80% of the present tests performed using first generation nasal samples clotted within six hours when *S. aureus* was present in the first generation test sample, i.e., directly from sources, such as a human source, an animal source, an environmental source (such as a tanning bed swab, or the like), or from a food source. If a clot forms, the clotted sample is monitored to determine whether a detectable signal is later generated in the clotted sample. This signal can be a change in color, the release of the indicator in the nutrient indicator, a change in pH produced by the metabolism of sugars, alcohol sugars, or amino acids, or some other detectable signal in the sample. Other detectable signals could include a change is light scattering in the clot, a change in viscosity, a change in optical density or conductivity that would indicate the presence of the target microbe.

To determine the effectiveness of the present method and mixture, a control study was performed involving sixty (60) defined samples titred to contain varying amounts of MRSA. Standard clones of MRSA were grown in trypticase soy broth (TSB), and were diluted by log 10 increments. The present invention test mixture was inoculated with a fixed amount (0.1 ml) of each the control samples. A first set of the inoculated test mixtures were incubated at 35° C., and second set of the inoculated test mixtures were incubated at 23° C. Of the sixty control test samples, positives for all MRSA were noted in five hours, forty-nine (49) were positive in four hours; thirty-six (36) were positive in three hours, and twenty-four (24) in two hours. Data detailing the relationship between the concentration of the inoculum, and incubation temperature was as follows:

| *S. aureus* CFU/ml | Clot at 35° C. | Clot at 23° C. |
|---|---|---|
| 7 log 10 | 2.0 hr | 3.0 hr |
| 6 log 10 | 3.0 hr | 3.0 hr |
| 5 log 10 | 4.0 hr | 4.0 hr |
| 4 log 10 | 6.0 hr | 7.0 hr |
| 3 log 10 | 10.0 hr | 11.5 hr |
| 2 log 10 | 15.0 hr | 21.0 hr |

The concentration of *S. aureus* within the clots were all at least 5 log 10.

An effective formulation for detecting the presence or absence of MRSA in a first generation sample of the type referred to herein is set forth below.

| Ingredients | Source | Gms/L |
|---|---|---|
| Mueller Hinton Broth | HiMedia | 8.00 |
| Yeast extract | France | 5.25 |
| Lithium chloride | Sigma | 5.00 |
| Trehalose | Canton | 12.00 |
| Phenol red | GSP | 0.018 |
| Maltose | Sunmalt, Japan | 3.00 |
| Mannitol | China | 5.00 |
| Amphotericin B | UK | 0.005 |
| Kinetin | Pharma world | 0.001 |
| Indole acetic acid | " | 0.005 |
| Gibberellic acid | — | 0.001 |
| IPTG | Inalco | 0.005 |
| Phenyl ethyl alcohol | Fluka | 1.500 ml |

-continued

| Ingredients | Source | Gms/L |
|---|---|---|
| Desfuroxime | Sigma | 0.0015 |
| Potassium phosphate | | 0.025 |
| Aztreonam | Glaxo | 0.006 |
| Colistin | Al-pharma | 0.005 |
| Cefoxitin | UK | 0.006 |
| Gentamicin | | 0.010 |
| Rabbit plasma | ID Bios | 50.00 |
| Fibrinogen | " | 11.33 |

In addition to the above described control study, a clinical study was performed using fifty samples. The samples were taken from a medical intensive care unit by culturing patient nares. The patients were not identified, nor were the results of any "standard" culture available (FDA protocol). The samples were plated on mannitol salt agar (MSA) using swabs. After plating the samples on MSA, the swabs were used to inoculate the test mixture. Clotting was looked for each hour for twenty-four hours. There were no false positives using the above formulation.

It will be appreciated that the test of this invention is significantly simpler to perform than the standard tests which are currently in use, as typified by the coagulase plasma procedure suggested by Remel Products, Thermo Fisher Scientific, Lenexa, Kans., U.S.A. The Remel procedure, which is approved by the FDA and appears in the Code of the Federal Register as an exempt test, requires a two step test for *S. aureus* wherein microbe colonies from the specimen are first grown in an agar menstrum and screened for suspected *S. aureus* colonies using a gram stain and catalase slide test before proceeding to a second coagulase test step. There are complications relating to this type of coagulase test, namely:

1) colonies for coagulase testing must not be picked, i.e., chosen by a skilled medically certified technologist, from media containing high concentrations of salt as false positive results may occur;

2) in the first step slide test procedure, the organism/saline suspension must be observed for auto-agglutination prior to the addition of the coagulase plasma to prevent a false positive test reading; and 3) false negative coagulase reactions may occur if the test culture is older that than 18-24 hours, of if there is scant growth.

While the invention has been described with respect to preferred embodiments, those skilled in the art will readily appreciate that various changes and/or modifications can be made to the invention.

What is claimed is:

1. A method for detecting the presence or absence of Methicillin Resistant *Staphylococcus Aureus* ("MRSA") in a first generation biological, food, or environmental specimen sample, said method comprising the steps of:

a) providing a powdered hydratable test mixture containing one or more growth promoting constituents that promote the growth of MRSA, at least one antibiotic component which will selectively inhibit the growth of Methicillin Susceptible *Staphylococcus Aureus* ("MSSA"), coagulase substrates operative to react with a coagulase enzyme system produced by pathogenic staphylococci in the first generation specimen, and at least one hydrolyzable substrate which MRSA can metabolize to produce a detectable signal in a coalescence formed in a container containing said specimen sample;

b) hydrating the test mixture in said container;

c) forming an admixture of said first generation specimen sample and said hydrated test mixture in said container;

d) incubating said admixture of said hydrated test mixture and said specimen sample in said container at temperatures in the range of about 20° C. to about 42° C.;

e) observing said admixture to note the presence or absence of coalescence of said admixture in said container; and f) monitoring any coalescence in said container for the presence or absence of said detectable signal wherein the presence of a detectable signal indicates the presence of MRSA and the absence of a detectable signal indicates the absence of MRSA in the specimen sample.

2. The method of claim 1 wherein the test mixture includes:

a) an effective amount of amino acids;

b) an effective amount of nitrogen sources;

c) an effective amount of salts;

d) an effective amount of vitamins;

e) an effective amount of calcium;

f) an effective amount of rabbit plasma;

g) an effective amount of the hydrolyzable substrate which MRSA can metabolize; and h) an effective amount of sugars, alcohol sugars, or amino acids, which MRSA can metabolize.

3. The method of claim 1 wherein said antibiotic component includes an effective amount of an anti-ribosomal antibiotic which will selectively kill MSSA in the specimen sample.

4. The method of claim 3 wherein said anti-ribosomal antibiotic is selected from the group consisting of: gentamicin, tobramycin, kanamycin, and mixtures thereof.

5. The method of claim 3 wherein said anti-ribosomal antibiotic is tobramycin.

6. The method of claim 1 wherein said specimen sample is a biological sample collected as a nasal swab, a lesion swab, a skin swab, or a throat swab.

7. The method of claim 1 wherein said specimen sample is an environmental sample collected as a tanning salon swab, a gym swab, a restaurant swab, or a hotel swab.

8. The method of claim 1, wherein the container is a test tube.

9. The method of claim 1, wherein the detectable signal is one or more of: a) a change in color; b) a release of an indicator from a nutrient indicator; c) a change in pH produced by metabolism of one or more of sugars, alcohol sugars, and amino acids; d) a change in light scattering in the clot coalescence; e) a change in viscosity of the clot coalescence; f) a change in optical density of the admixture; and g) a change in conductivity of the admixture.

* * * * *